US00PP35252P2

(12) United States Plant Patent
Ployphommas

(10) Patent No.: US PP35,252 P2
(45) Date of Patent: Jul. 4, 2023

(54) ***AGLAONEMA* PLANT NAMED 'SUMALEE'**

(50) Latin Name: *Aglaonema rotundum*
Varietal Denomination: Sumalee

(71) Applicant: Paiboon Ployphommas, Nong Sam Wang (TH)

(72) Inventor: Paiboon Ployphommas, Nong Sam Wang (TH)

( * ) Notice: Subject to any disclaimer, the term of this patent is extended or adjusted under 35 U.S.C. 154(b) by 0 days.

(21) Appl. No.: 17/803,659

(22) Filed: Sep. 26, 2022

(51) Int. Cl.
*A01H 5/12* (2018.01)
*A01H 6/10* (2018.01)

(52) U.S. Cl.
USPC ..... Plt./376

(58) Field of Classification Search
USPC ..... Plt./373, 376
See application file for complete search history.

(56) References Cited

PUBLICATIONS

Facebook page for Rare plants Philippines, picture of *Aglaonema* Sumalee Tricolors. https://m.facebook.com/permalink.php?id=115734483681870&story_fbid=176495557605762. 2 pages. (Year: 2021).*

* cited by examiner

*Primary Examiner* — Karen M Redden
(74) *Attorney, Agent, or Firm* — Samuel R. McCoy, Jr.

(57) ABSTRACT

'Sumalee' is a new and distinctive *Aglaonema* plant which is characterized by multicolored foliage with vibrant pink veins, born on pink petioles, and the stability of all characteristics from generation to generation. The new variety is typically produced as an indoor ornamental plant.

4 Drawing Sheets

Latin name of the genus and species: The Latin name of the genus and species of the novel variety disclosed herein is *Aglaonema rotundum.*

Variety denomination: The inventive variety of *Aglaonema* disclosed herein has been given the variety denomination 'Sumalee'.

BACKGROUND OF THE INVENTION

Parentage: The claimed plant originated as an induced, whole-plant mutation. In 2017, the inventor initiated meristematic tissue culture propagation of an unnamed *Aglaonema rotundum* plant (not patented) at his commercial plant tissue culture laboratory in Nong Sam Wang, a subdistrict in the Nong Suea district of Pathum Thani province, Thailand. A plurality of parent plant cultures were treated with a combination of 1 mg/L of benzyl adenine (BA) and 0.1 mg/L of 2,4-dichlorophenoxyacetic acid (2,4-D) to induce mutation. Once the cultures were callused, they were treated with 1 mg/L benzyl adenine (BA) to induce foliar shoot development and growth. In October of 2018, once foliage developed, the inventor observed one culture that exhibited unique multicolored foliage characteristics relative to the parent. Said culture was deflasked and grown to a mature size to confirm the distinctness and stability of the characteristics first observed. In October of 2019, after further evaluation, it was determined that the new plant exhibited unique foliage coloration that would prove favorable for commercial marketability. The new variety was given the denomination 'Sumalee'.

Asexual Reproduction: Asexual reproduction of 'Sumalee', by way of leaf cuttings, was first performed in April at the inventor's greenhouse in Nong Sam Wang, a subdistrict in the Nong Suea district of Pathum Thani province, Thailand. 'Sumalee' was subsequently reproduced by way of meristematic tissue culture propagation as well. Five successive generations so produced have shown that the unique features of the instant cultivar are stable and reproduced true to type.

SUMMARY OF THE INVENTION

The cultivar 'Sumalee' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Aglaonema* cultivar 'Sumalee'. These traits, in combination, distinguish 'Sumalee' as a new and distinct cultivar.

1. *Aglaonema* 'Sumalee' exhibits petioles that are colored light red on the abaxial surface, generally appearing as a pink coloration; and
2. *Aglaonema* 'Sumalee' exhibits prominent red veins on both the adaxial and abaxial foliar surfaces, generally appearing as a vibrant pink coloration; and
3. *Aglaonema* 'Sumalee' exhibits a dark yellow-green adaxial foliar surface which is centrally and irregularly blotched with an array of colors ranging from very light orange-white and flecked with yellow-green to light yellow-green and suffused or flecked with very light orange-white to orange-white blotches that are heavily suffused with red and generally appearing as a vibrant pink coloration; and
4. *Aglaonema* 'Sumalee' exhibits a very dark yellow-green abaxial laminar surface which is centrally and irregularly blotched with red, generally appearing as a vibrant pink coloration.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
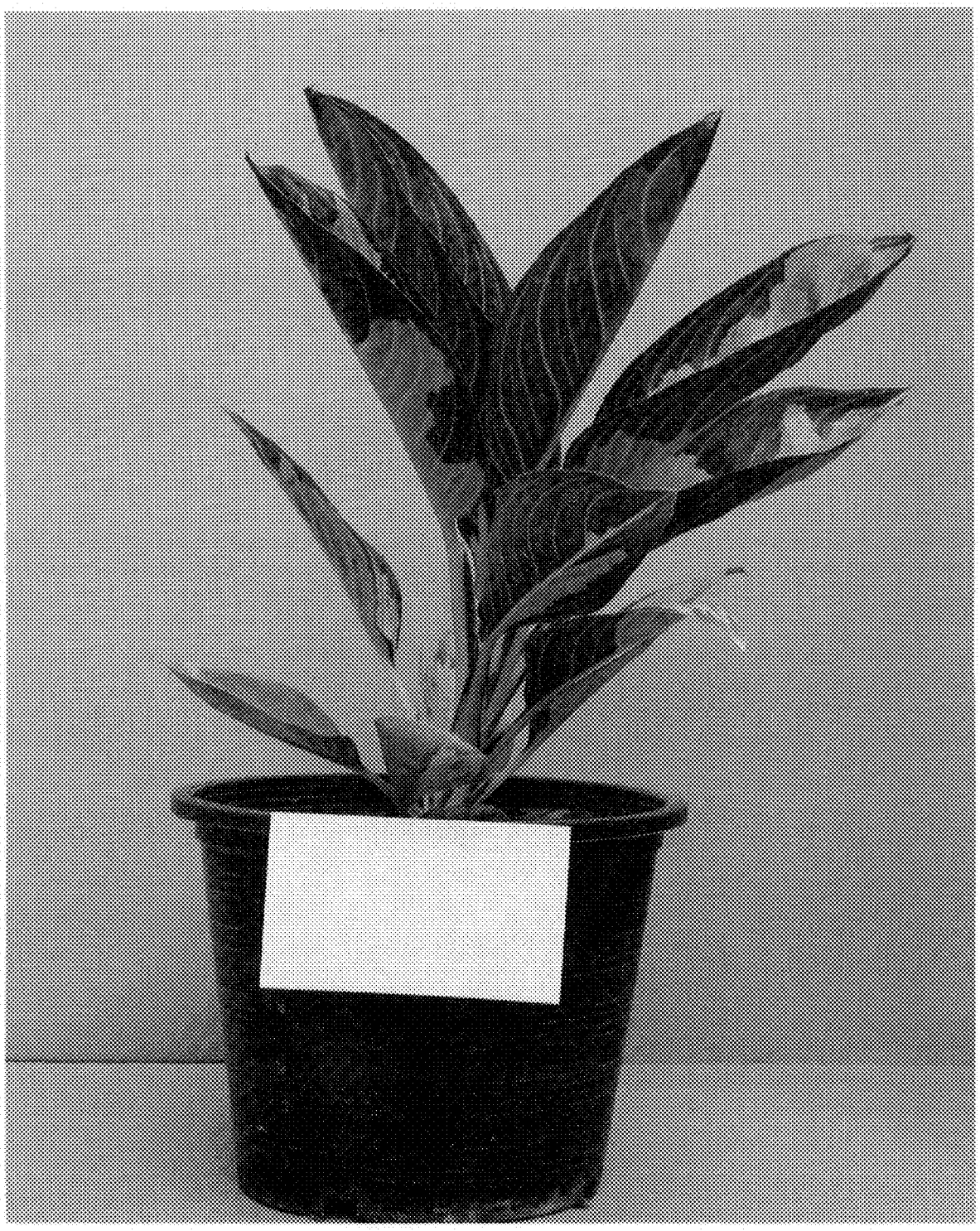
FIG. 1 shows, as nearly true as it is reasonably possible to make the same in color illustrations of this type, an exemplary plant of the new cultivar, 'Sumalee'. The plant shown is approximately 18 months old from a rooted cutting, potted into a 20 cm nursery container, grown in a greenhouse in Nong Sam Wang, a subdistrict in the Nong Suea district of Pathum Thani province, Thailand.
Figure 2:
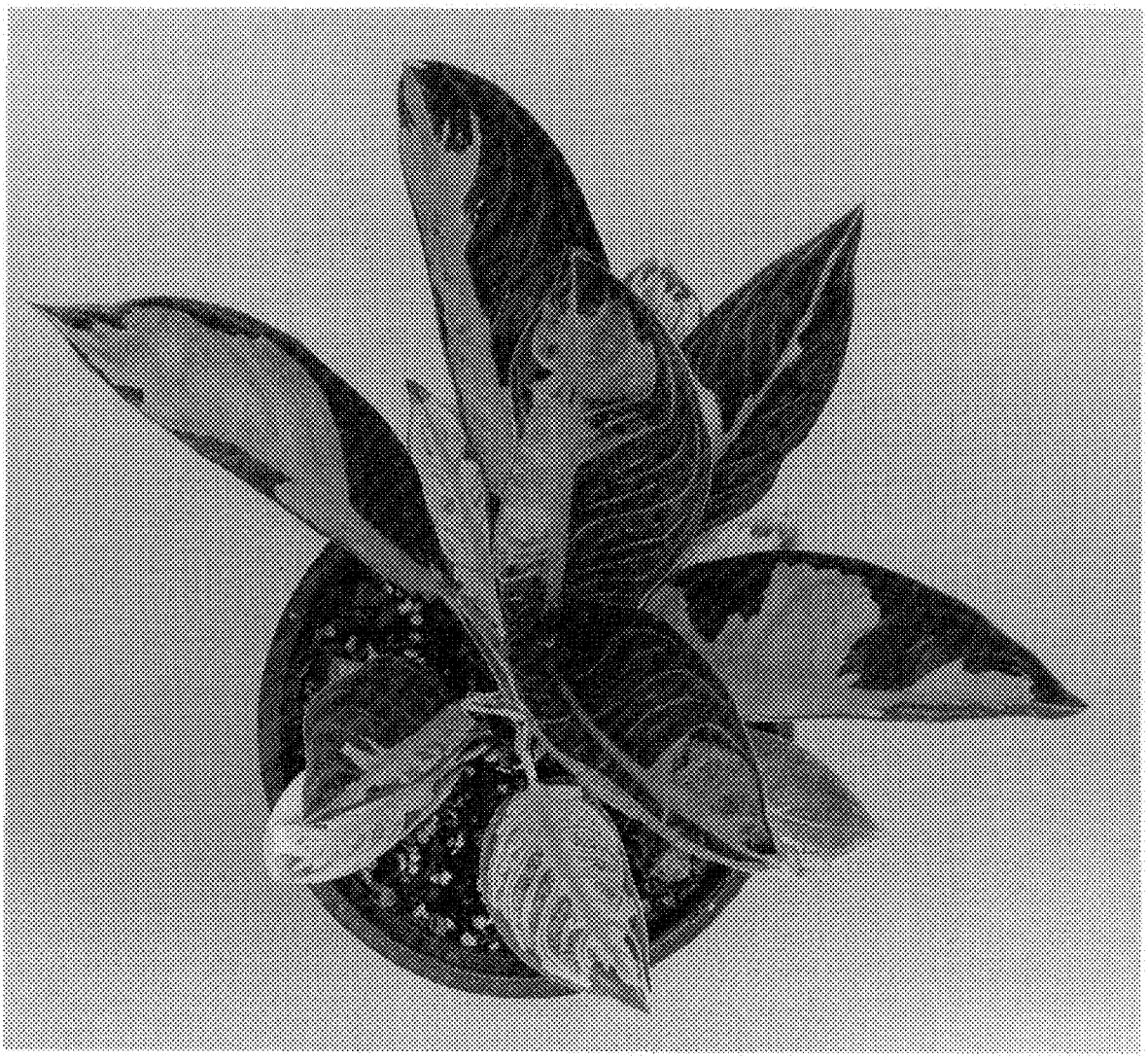
FIG. 2 shows, as nearly true as it is reasonably possible to make the same in color illustrations of this type, a top perspective showing the foliage arrangement of the claimed plant.
Figure 3:
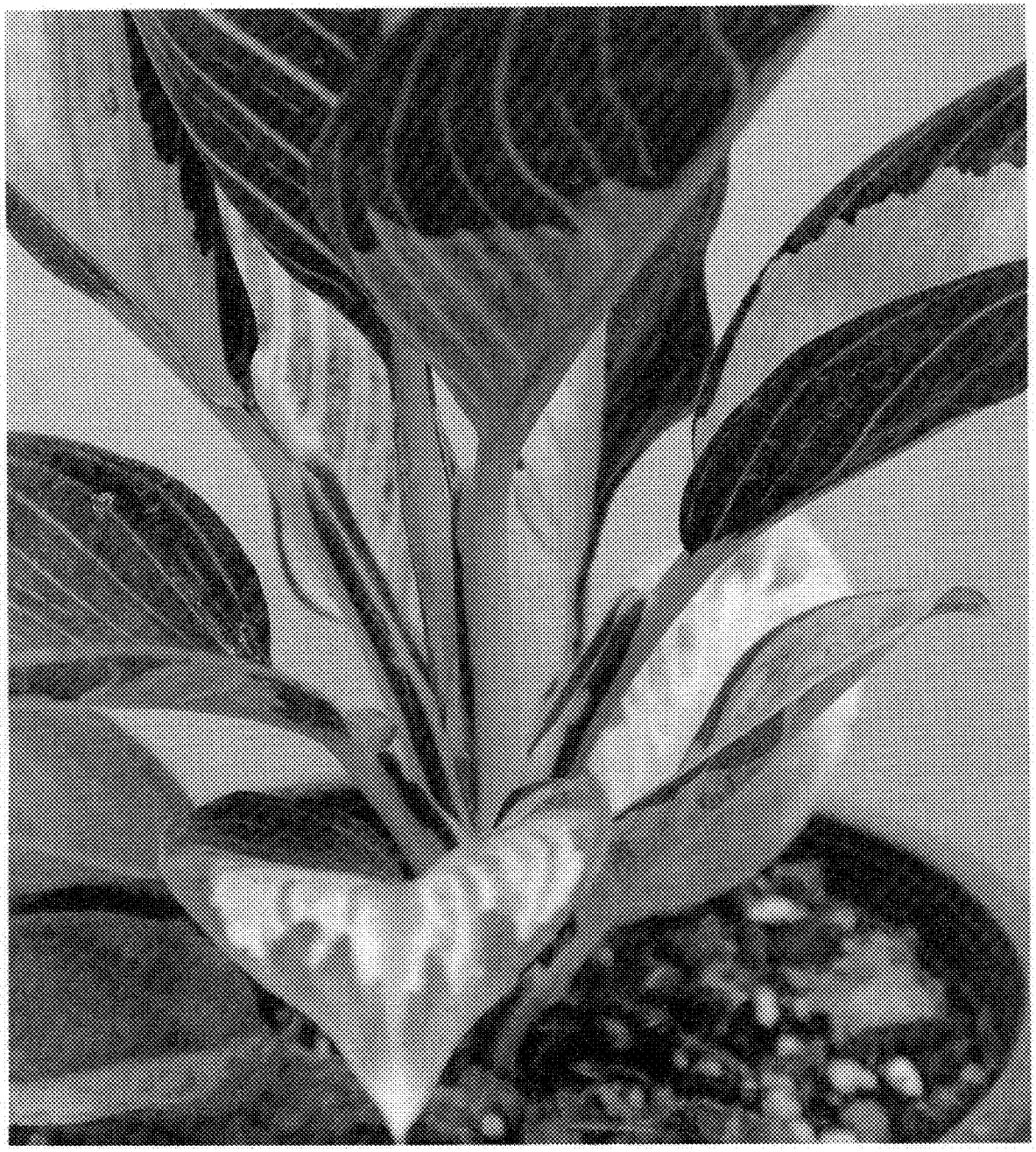
FIG. 3 shows, as nearly true as it is reasonably possible to make the same in color illustrations of this type, the petioles of the claimed plant.
Figure 4:
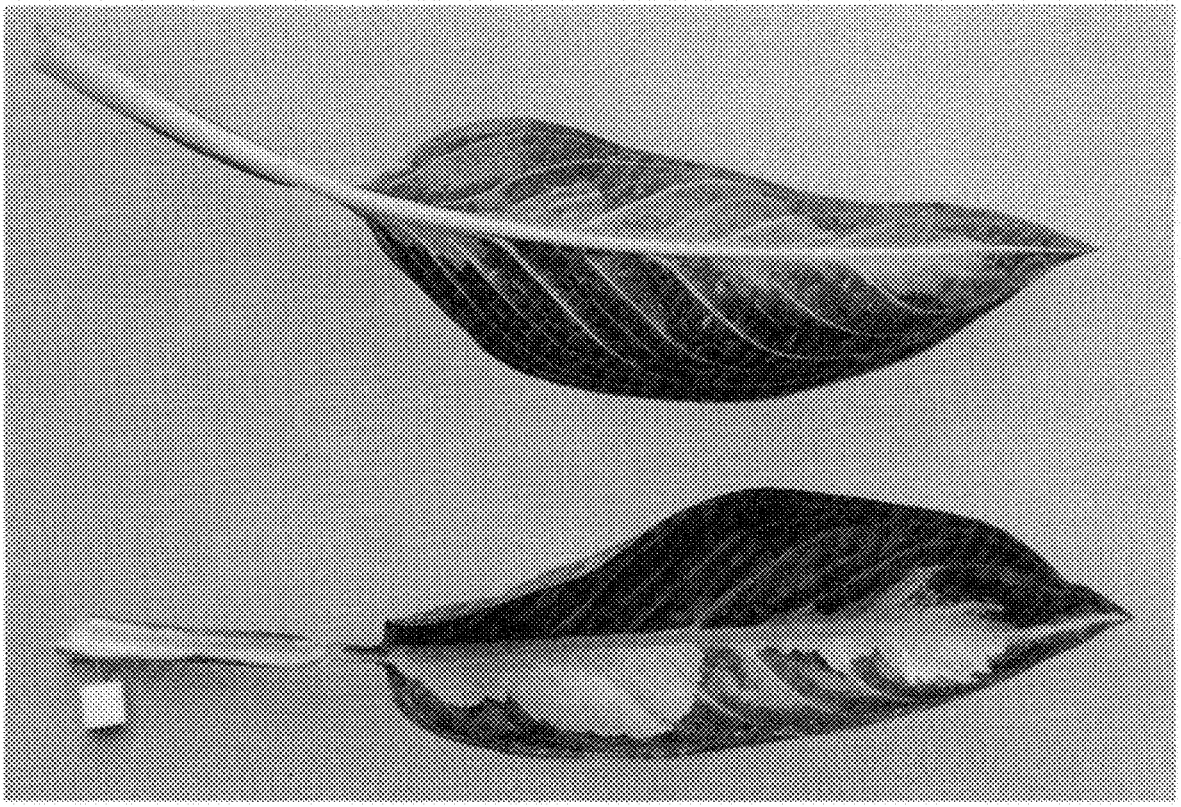
FIG. 4 shows, as nearly true as it is reasonably possible to make the same in color illustrations of this type, the adaxial and abaxial surfaces of the mature foliage of the claimed plant.

The following observations and measurements made in August of 2022 describe an 18-month-old 'Sumalee' plant grown in a 20 cm nursery container at commercial greenhouse in Nong Sam Wang, a subdistrict in the Nong Suea district of Pathum Thani province, Thailand. Plants were produced using conventional greenhouse production protocols for *Aglaonema* which consisted of growing under 70-percent shade cloth, regular overhead irrigation every two days, and slow-release granular fertilizer applications at 4-month intervals, approximately. Preventative applications of Imadacloprid and Metalyx pesticides were utilized to prevent insect infestations and fungal infections. No photoperiodic treatments or artificial light was given to the plants.

Those skilled in the art will appreciate that certain characteristics will vary with older or, conversely, with younger plants. 'Sumalee' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart,* The Royal Horticultural Society, London, 1986 (third edition).

A botanical description of 'Sumalee' and comparisons with the parent and the most similar variety of common knowledge are provided below.

General plant description:

*Growth habit*.—Clump forming; upright with foliage arising directly from the base of each clump.

*Plant profile*.—Upright, globular.

*Height*.—25.6 cm.

*Width*.—Average 23.2 cm in width.

*Plant vigor*.—Moderately vigorous.

*Propagation*.—Method — Meristematic tissue culture. Time to initiate roots — Approximately 8 weeks to initiate roots at approximately 25 degrees Centigrade. Crop time — Approximately 18 to 20 weeks to produce a well-rooted 10 cm container from a rooted cutting.

*Environmental tolerances*.—Moderately high tolerance to rain; low to moderate tolerance to wind; tolerant of temperatures to at least 40 degrees Celsius. Cold hardy to USDA Hardiness Zone 10.

*Pest resistance and susceptibility*.—Plants have not been observed to be any more or less susceptible or resistant to pathogens and pests common to *Aglaonema* sp.

Root system:

*Branching*.—Moderately branched.

*Density*.—Moderately dense.

*Distribution*.—Roots are shallow to moderately deep.

*Texture*.—Fleshy; smooth; lacking root hairs.

*Color*.—Greyed-yellow, nearest to RHS 161D.

Stems:

*Branching characteristics*.—Clumping plant with leaves emerging directly from the base of the plant; no main stems or lateral branching.

Foliage:

*Arrangement*.—Spiraled.

*Division*.—Simple.

*Attachment*.—Petiolate.

*Quantity of leaves per shoot*.—12.

*Quantity of shoots per plant*.—3.

*Quantity of leaves per plant*.—36.

*Lamina*.—Shape — Ovate. Apex — Acute. Base — Short attenuate. Aspect — Concaved. Attitude — Upright and outward, at an approximate angle of 45 to 60 degrees from horizontal. Dimensions — 15.27 cm long and 7.13 cm wide. Margin — Entire; very slight coarse undulation. Texture and luster, adaxial surface — Smooth, glabrous, and slightly glossy. Texture and luster, abaxial surface — Smooth, glabrous, and matte. Juvenile color, adaxial surface — Yellow-green, nearest to in between RHS 146A and 147A. Centrally and irregularly blotched with a varying array of colors. On some leaves, the blotches are orange-white, RHS 158D, and lightly to heavily flecked with yellow-green, nearest to RHS 147A. Some leaves exhibit blotches that are green-yellow, RHS 1C, and either suffused with orange-white or lightly to moderately flecked with orange-white, nearest to RHS 158D. On other leaves, the blotches are a mixture of orange-white and green-yellow, nearest to RHS 158D and 1C, and lightly to heavily suffused with red, nearest to RHS 51A, radiating outward from the main and lateral veins, eventually coalescing to form a red blotch, nearest to RHS 51A. The degree to which laminas are blotched is highly variable from leaf to leaf, with some leaves exhibiting a small amount of central blotching and other leaves exhibiting blotches that cover the majority of the laminal surface. Juvenile color, abaxial surface — Yellow-green, nearest to in between RHS 147A and 148A; centrally and irregularly blotched red, nearest to RHS 51C, and lightly suffused with yellow-green, nearest to RHS 148A. The degree to which laminas are blotched is highly variable from leaf to leaf, with some leaves exhibiting a small amount of central blotching and other leaves exhibiting blotches that cover the majority of the laminal surface. Mature color, adaxial surface — Yellow-green, nearest to in between RHS 146A and 147A. Centrally and irregularly blotched with a varying array of colors. On some leaves, the blotches are orange-white, RHS 158D, and lightly to heavily flecked with yellow-green, nearest to RHS 147A. Some leaves exhibit blotches that are green-yellow, RHS 1C, and either suffused with orange-white or lightly to moderately flecked with orange-white, nearest to RHS 158D. On other leaves, the blotches are a mixture of orange-white and green-yellow, nearest to RHS 158D and 1C, and lightly to heavily suffused with red, nearest to RHS 51A, radiating outward from the main and lateral veins, eventually coalescing to form a red blotch, nearest to RHS 51A. The degree to which laminas are blotched is highly variable from leaf to leaf, with some leaves exhibiting a small amount of central blotching and other leaves exhibiting blotches that cover the majority of the laminal surface. Mature color, abaxial surface — Yellow-green, nearest to in between RHS 147A and 148A; centrally and irregularly blotched red, nearest to RHS 51C, and lightly suffused with yellow-green, nearest to RHS 148A. The degree to which laminas are blotched is highly variable from leaf to leaf, with some leaves exhibiting a small amount of central blotching and other leaves exhibiting blotches that cover the majority of the laminal surface. Venation — Vein pattern — Arcuate. Vein color, adaxial surface — Main veins are red, nearest to RHS 51A, and fading lighter at both the base and apex, nearest to RHS 50D. Lateral veins are orange-white, nearest to RHS 159D, and strongly suffused with red, nearest to RHS 50B. Vein color, abaxial surface — Main veins are red, nearest to RHS 50D. Lateral veins are red, nearest to RHS 50D, and lightly to strongly suffused with a darker shade of red, nearest to RHS 50B.

*Petiole*.—Length — Approximately 6.5 cm. Width — Approximately 0.85 cm, including the petiole wings, at the proximal end and 0.4 cm at the distal end. Strength — Moderately strong. Texture — Glabrous. Luster — Slightly glossy. Color, adaxial surface — Orange-white, nearest to RHS 159D, and progressively suffused with red, RHS 50D, distally; irregularly margined with greyed-green, RHS 189A, along the petiole wings. The portion of the petiole between the petiole wings and lamina is irregularly blotched with a combination of red, RHS 50B, and yellow-green, nearest to in between RHS 146A and 147A. Color, abaxial surface — Red, nearest to RHS 50D; petiole wings are yellow-green, nearest to in between RHS 146A and 147A, and flecked with orange-white, nearest to RHS 159D, and lightly suffused with red-purple, nearest to RHS 62C. Petiole wings — General Description — Two petiole wings are present at the base of each petiole. Length — Approximately 5.4 cm. Width — Approximately 0.4 cm at the base. Margins — Entire; involute; lightly undulated. Texture and luster — Glabrous and very slightly glossy. Color, adaxial surface — Orange-white, nearest to RHS 159D, progressively suffused with red, RHS 50D, distally; irregularly margined with greyed-green, RHS 189A, at the petiole wings. Color, abaxial surface — Yellow-green, nearest to in between RHS 146A and 147A, and flecked with orange-white, nearest to RHS 159D; lightly suffused with red, nearest to RHS 50D.

Inflorescence: No flowering has been observed to date.

Flower buds: No flowering has been observed to date.

Flowers: No flowering has been observed to date.

Reproductive organs: No flowering has been observed to date.

Seed and fruit: Seed production has not been observed.

Comparisons With the Parent

Plants of the new cultivar 'Sumalee' may be distinguished from the parent, an unnamed *Aglaonema rotundum* plant (not patented), which is also the most similar commercial comparator known to the inventor, by the characteristics described in Table 1.

TABLE 1

| Characteristic | 'Sumalee' | The parent. |
|---|---|---|
| General coloration of the petioles. | Red, generally appearing as pink. | Green. |
| Presence of multicolored blotches on the adaxial foliar surface. | Present; prominent. | Absent. |
| Presence of red blotches on the abaxial foliar surface. | Present; prominent. | Absent. |

Comparisons With the Most Similar Commercial Variety

Plants of the new cultivar 'Sumalee' may be distinguished from the most similar commercial comparator know to the inventor, *Aglaonema* 'Pride of Sumatra' (not patented), by the characteristics described in Table 2.

TABLE 2

| Characteristic | 'Sumalee' | 'Pride of Sumatra' |
|---|---|---|
| Plant height. | Taller than 'Pride of Sumatra'. | Shorter than 'Sumalee'. |
| Foliage shape. | Ovate. | Elliptic. |
| Foliage luster. | Slightly glossy. | Very glossy. |
| Expression of the foliar color patterns: adaxial and abaxial surfaces. | Random: irregular: highly variable from leaf to leaf. | Conspicuously patterned; consistent front leaf to leaf. |
| Presence of multicolored blotches on the foliar surfaces. | Present: prominent. | Absent. |

That which is claimed is:

1. A new and distinct variety of *Aglaonema* plant named 'Sumalee', substantially as described and illustrated herein.

* * * * *